(12) United States Patent
Sujith

(10) Patent No.: US 11,135,135 B2
(45) Date of Patent: Oct. 5, 2021

(54) PILL DISPENSING CANISTER

(71) Applicant: Yesudasan Sujith, Shreveport, LA (US)

(72) Inventor: Yesudasan Sujith, Shreveport, LA (US)

( * ) Notice: Subject to any disclaimer, the term of this patent is extended or adjusted under 35 U.S.C. 154(b) by 0 days.

(21) Appl. No.: 16/650,909

(22) PCT Filed: Sep. 26, 2018

(86) PCT No.: PCT/US2018/052995
§ 371 (c)(1),
(2) Date: Mar. 26, 2020

(87) PCT Pub. No.: WO2019/067646
PCT Pub. Date: Apr. 4, 2019

(65) Prior Publication Data
US 2020/0289375 A1    Sep. 17, 2020

Related U.S. Application Data

(60) Provisional application No. 62/563,152, filed on Sep. 26, 2017.

(51) Int. Cl.
*G16H 20/13* (2018.01)
*A61J 7/04* (2006.01)
*A61J 7/00* (2006.01)

(52) U.S. Cl.
CPC .......... *A61J 7/0454* (2015.05); *A61J 7/0084* (2013.01); *A61J 7/0427* (2015.05); *G16H 20/13* (2018.01)

(58) Field of Classification Search
CPC ......... B65D 83/04; A61J 7/02; A61J 2200/70; B65B 35/08; B65B 57/20; A61M 2205/13; A61M 2205/609; G16H 20/13; G16H 20/17
See application file for complete search history.

(56) References Cited

U.S. PATENT DOCUMENTS

| 5,522,525 | A | 6/1996 | McLaughlin et al. |
| 9,037,291 | B2* | 5/2015 | Terzini ............... B65B 35/08 |
| | | | 700/236 |
| 9,682,016 | B1 | 6/2017 | Balasubramanian et al. |
| 2005/0269346 | A1 | 12/2005 | Limback et al. |

(Continued)

OTHER PUBLICATIONS

International Search Report Corresponding to PCT/US2018/052995 dated Dec. 11, 2018.

(Continued)

*Primary Examiner* — Gene O Crawford
*Assistant Examiner* — Ayodeji T Ojofeitimi
(74) *Attorney, Agent, or Firm* — Holoubek Patent Law, LLC; Charlotte Holoubek

(57) ABSTRACT

A pill dispending canister mountable onto a pill packaging device comprising a hopper, a bulk dispenser, and a discrete dispenser. The hopper preferably includes a reservoir and an initial passage. The bulk dispenser preferably includes a bulk dispensing base, a bulk dispensing disc, a bulk dispensing motor, a pill exit chute, and bulk dispensing sensor. The discrete dispenser preferably includes a discrete dispensing base, a pill sorter, a discrete dispensing disc, a discrete dispensing motor, a pill drop chute, a pill jam sensor, a discrete pill sensor, a pill gate, a gate motor, and a control board.

19 Claims, 19 Drawing Sheets

(56) References Cited

U.S. PATENT DOCUMENTS

| | | |
|---|---|---|
| 2010/0264158 A1 | 10/2010 | van Ooyen et al. |
| 2011/0146213 A1 | 6/2011 | Terzini |
| 2011/0278195 A1 | 11/2011 | Giocastro |
| 2014/0110424 A1 | 4/2014 | Kim |
| 2016/0346167 A1 | 12/2016 | Littman et al. |
| 2017/0270274 A1 | 9/2017 | Garcia et al. |
| 2019/0092500 A1 | 3/2019 | Sujith |

OTHER PUBLICATIONS

Written Opinion Corresponding to PCT/US2018/052995 dated Dec. 11, 2018.

\* cited by examiner

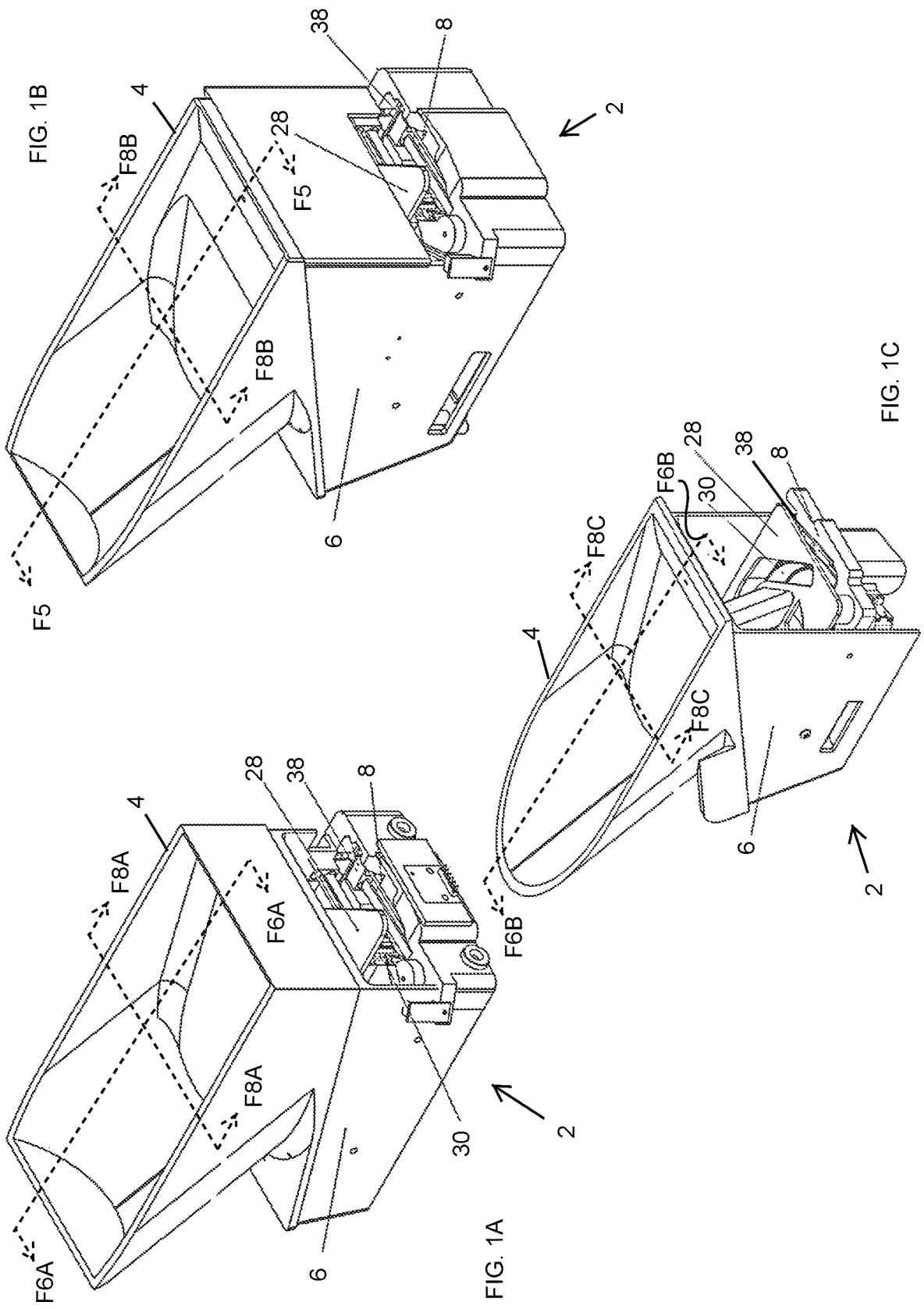

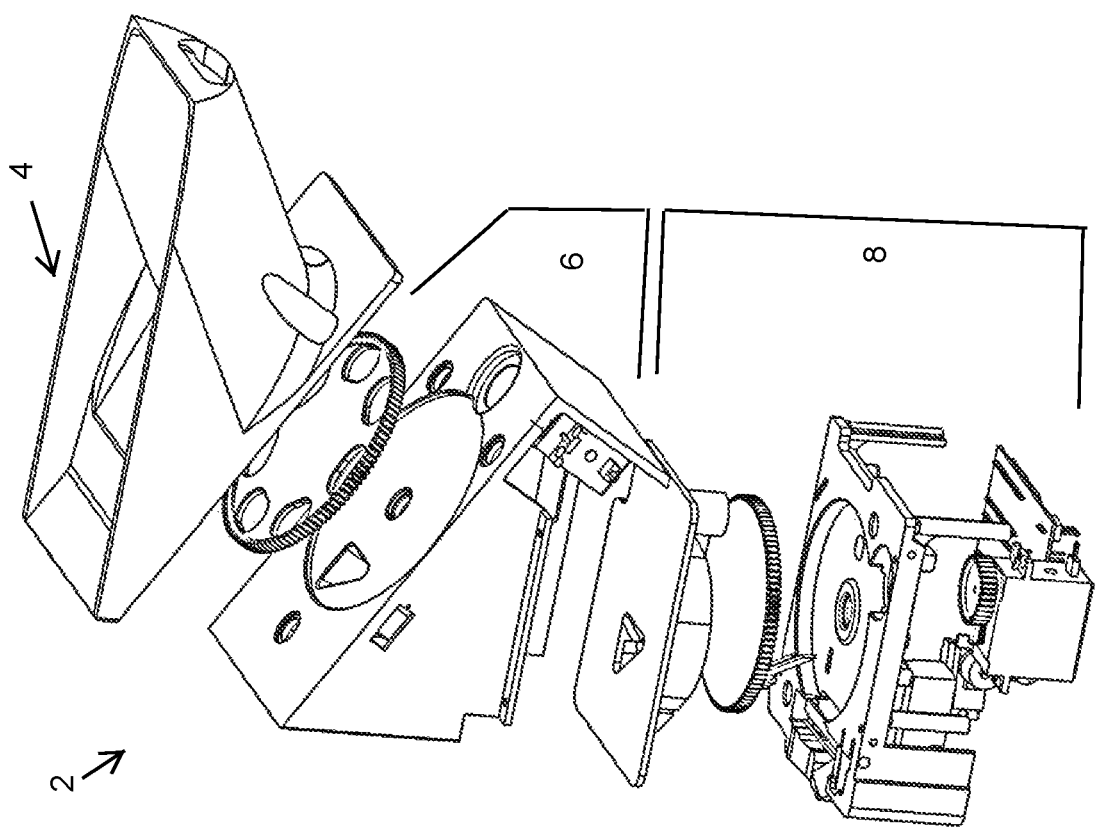
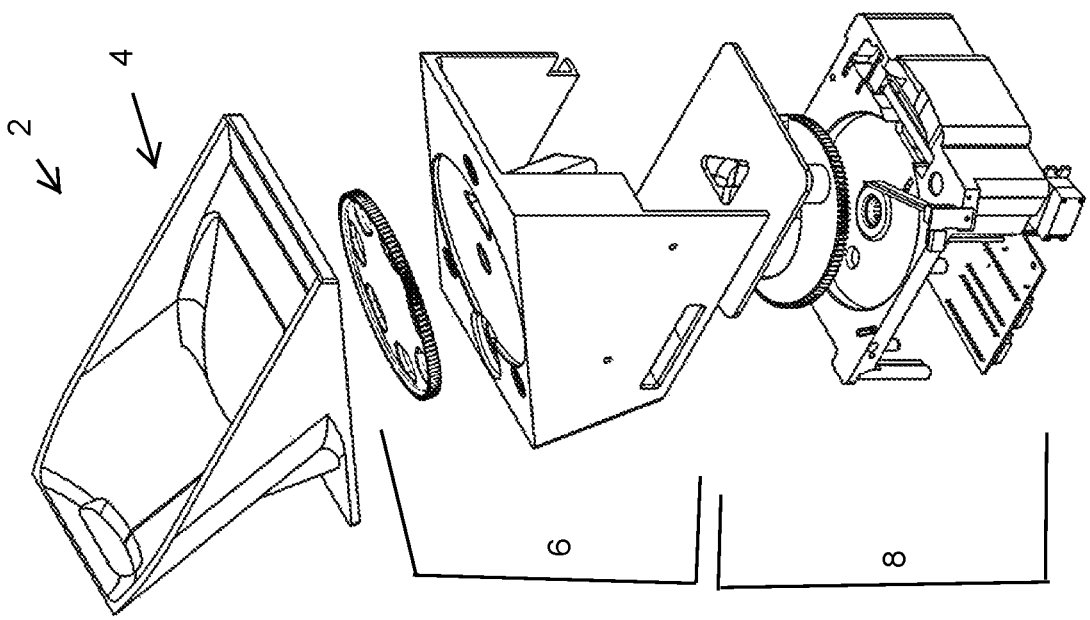

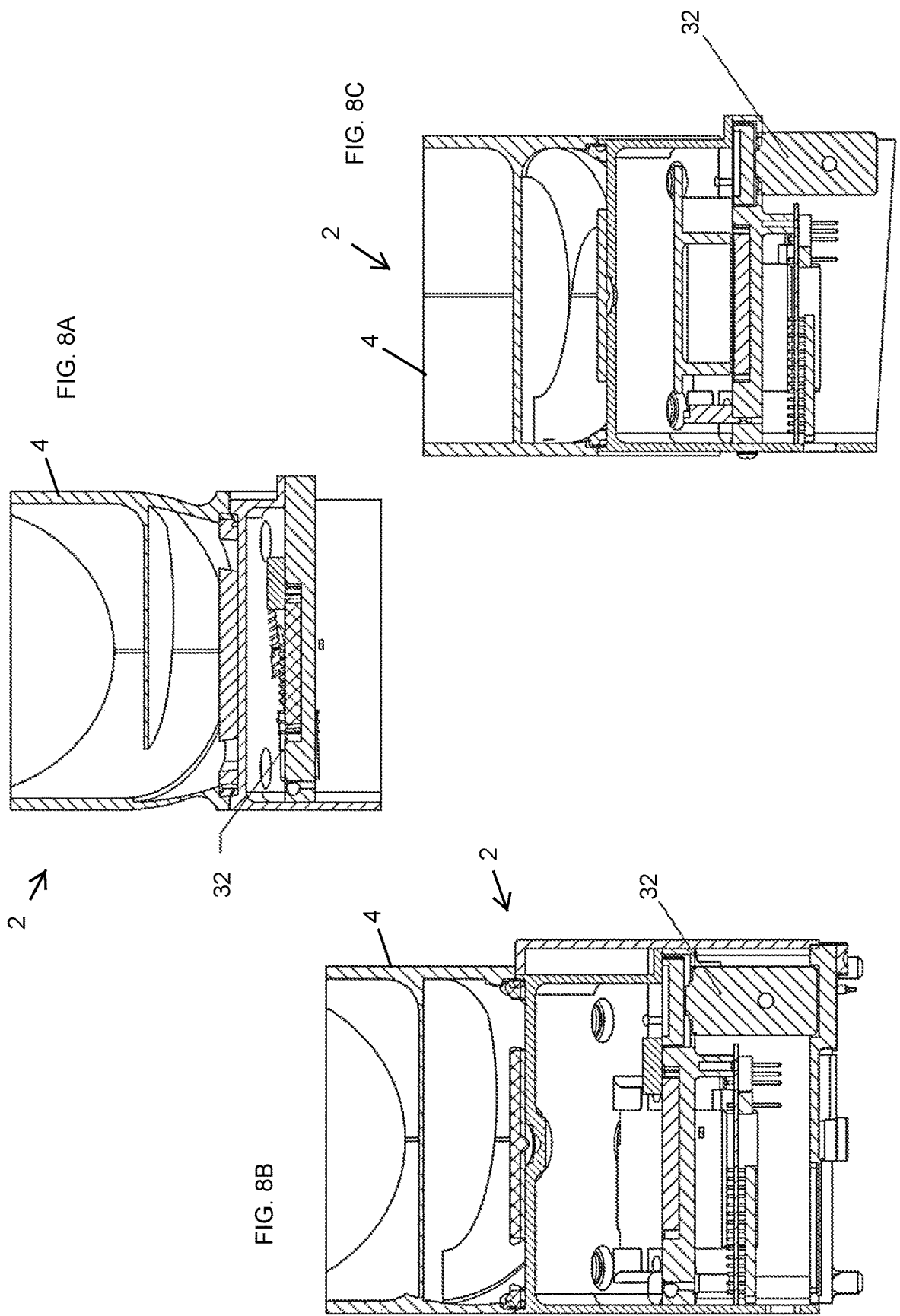

FIG. 11A
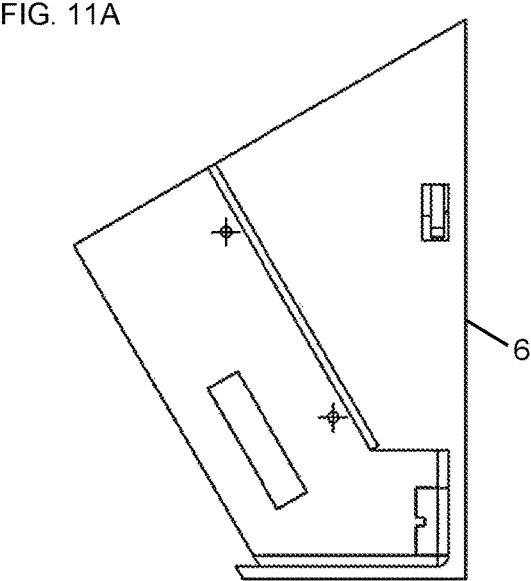
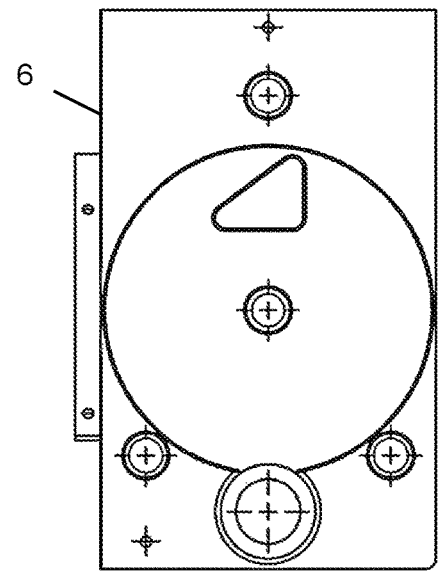
FIG. 11B
FIG. 11C
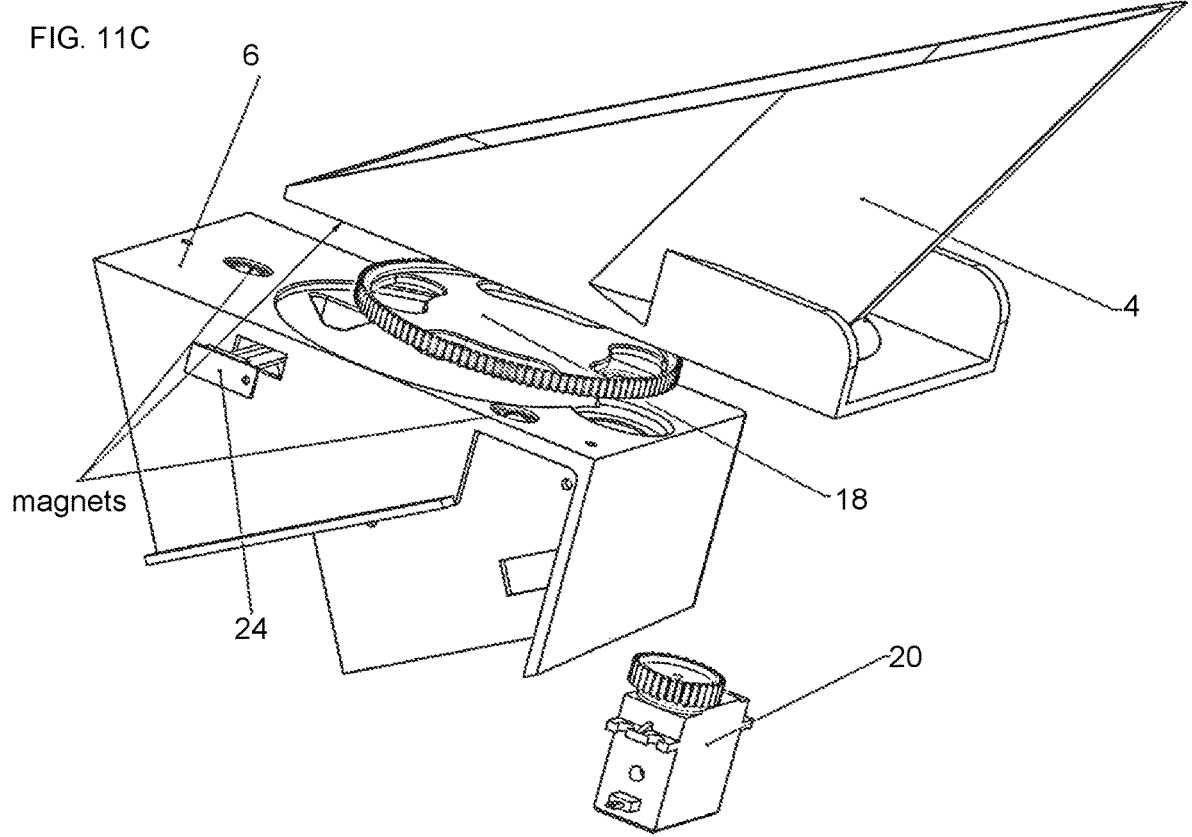

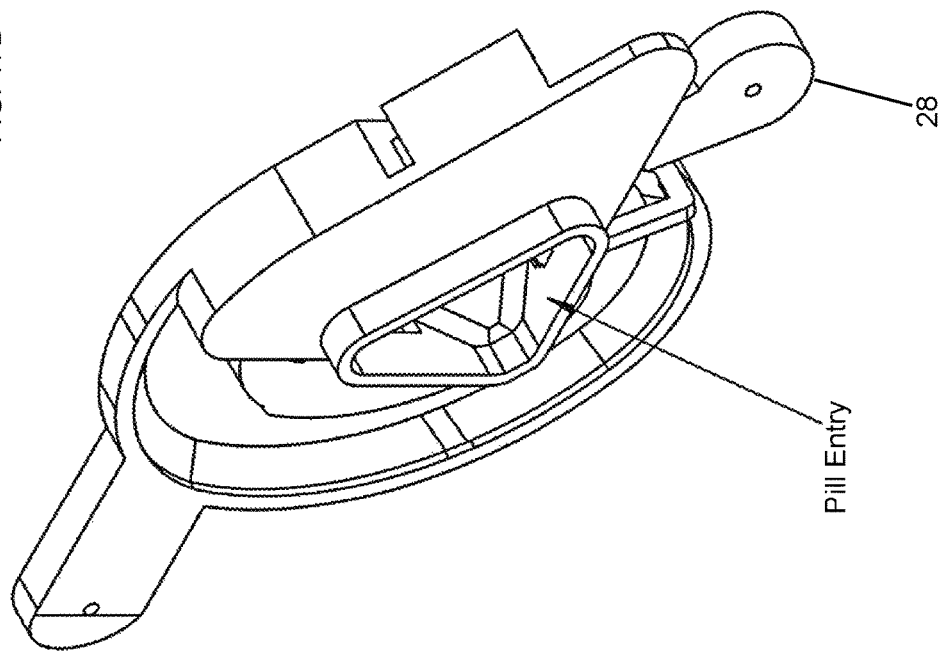
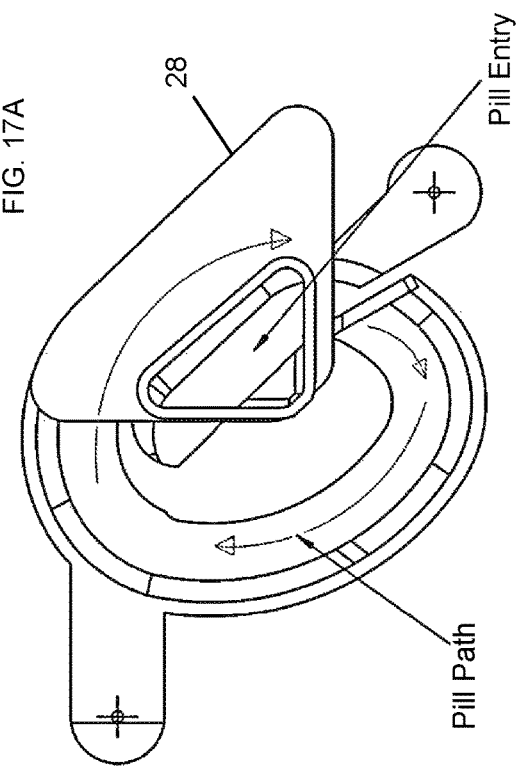
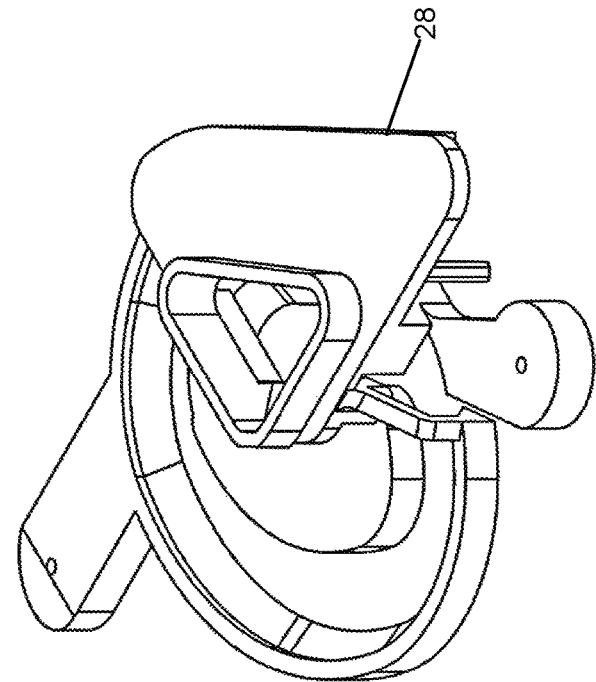

PILL DISPENSING CANISTER

CROSS REFERENCE TO RELATED APPLICATIONS/PRIORITY

The present invention claims priority to United States Provisional Patent Application No. 62/563,152 filed Sep. 26, 2017, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND OF THE INVENTION

There are many pharmacies, hospitals, and Long Term Care facilities where it is desired to individually package unit doses of medications. This is accomplished by placing the medication (normally in pill, tablet or capsule form and hereinafter the term "pill" shall mean any of tablet, capsule, caplet, geltab, gelcaps, and other forms of oral solid medication) in packaging such as a strip packages and heat seal the package. Previous methods of packaging pills had many deficiencies. The inventor has described a novel pill packaging machine in U.S. patent application Ser. No. 16/141,250, filed Sep. 25, 2018, such patent application being incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

Current pill packaging technology suffers from deficiencies of, among other things, failing to successfully, quickly, and reliably load a desired number of pill(s) at a time into the pill packaging machines, in a manner that requires minimal human labor. Though there is a long felt need for addressing these problems, no solution has yet been presented by those of ordinary skill in the art. For the foregoing reasons, there is a pressing, but seemingly irresolvable need for an improved pill dispensing canister.

SUMMARY OF THE INVENTION

Wherefore, it is an object of the present invention to overcome the above mentioned shortcomings and drawbacks associated with the current technology. The present invention is directed to methods and apparatuses that satisfy the above shortcomings and drawbacks. The dispensing canister preferably comprises a hopper, connected to a bulk dispenser, connected to a discrete dispenser, to carry pills from the hopper, through the bulk dispenser, and through the discrete dispenser to dispense pills, one at a time, in a controlled manner.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are to scale for one or more embodiments, though such scale is not necessarily required, with emphasis also being placed on illustrating the principles of the invention. The invention will now be described, by way of example, with reference to the accompanying drawings in which:

FIGS. 1A-1C re a front left top isometric views of first (FIG. 1A), second (FIG. 1B), and third (FIG. 1C) embodiments of a pill dispensing canister according to the presently claimed invention;

FIGS. 3A and 3B are exploded front left top (FIG. 3A) and back right top (FIG. 3B) views of the pill dispensing canister in FIG. 1B;

FIGS. 8A, 8B, and 8C are cross sectional views of the pill dispensing canisters in FIGS. 1A, 1B, and 1C respectively, along the sectional lines F8A, F8B, and F8C respectively;

FIGS. 11A and 11B are side and top plan views of the bulk dispensing base of the dispensing canister of FIG. 1C, and FIG. 11C is an exploded view of the bulk dispenser and the hopper of the dispensing canister of FIG. 1C;

FIGS. 17A-17C are different isometric views of a smaller pill sized pill sorter;

DETAILED DESCRIPTION OF THE PREFERRED EMBODIMENTS

Figure 2B:
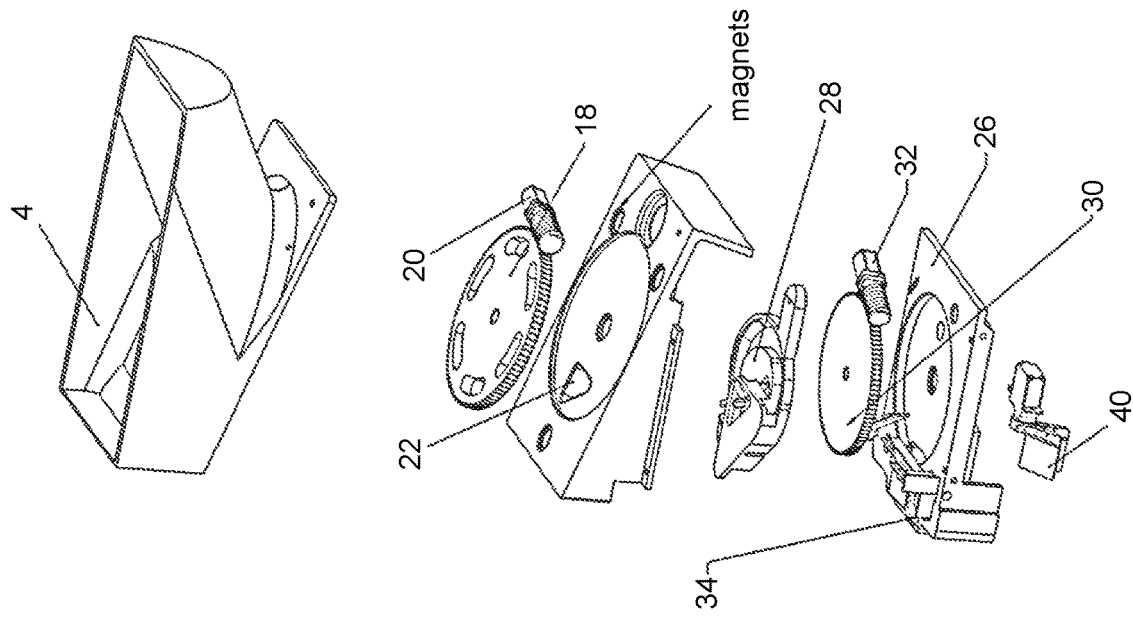
FIGS. 2A and 2B are exploded front left top (FIG. 2A) and back right top (FIG. 2B) views of the pill dispensing canister in FIG. 1A.
Figure 2A:
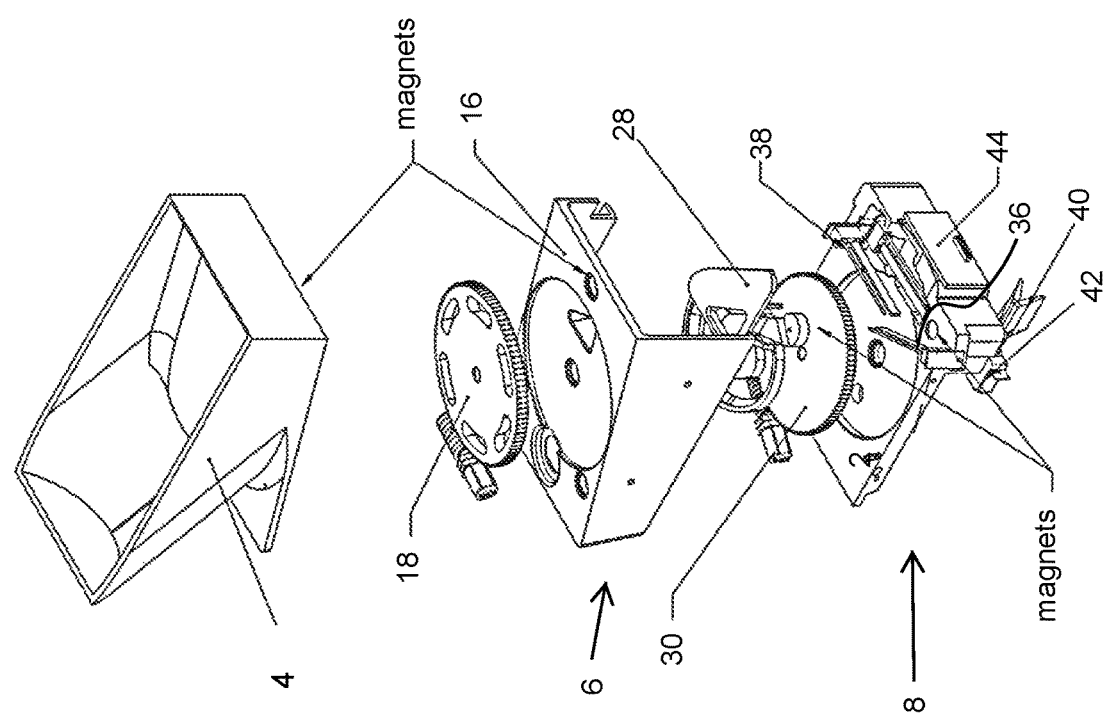
Figure 4B:
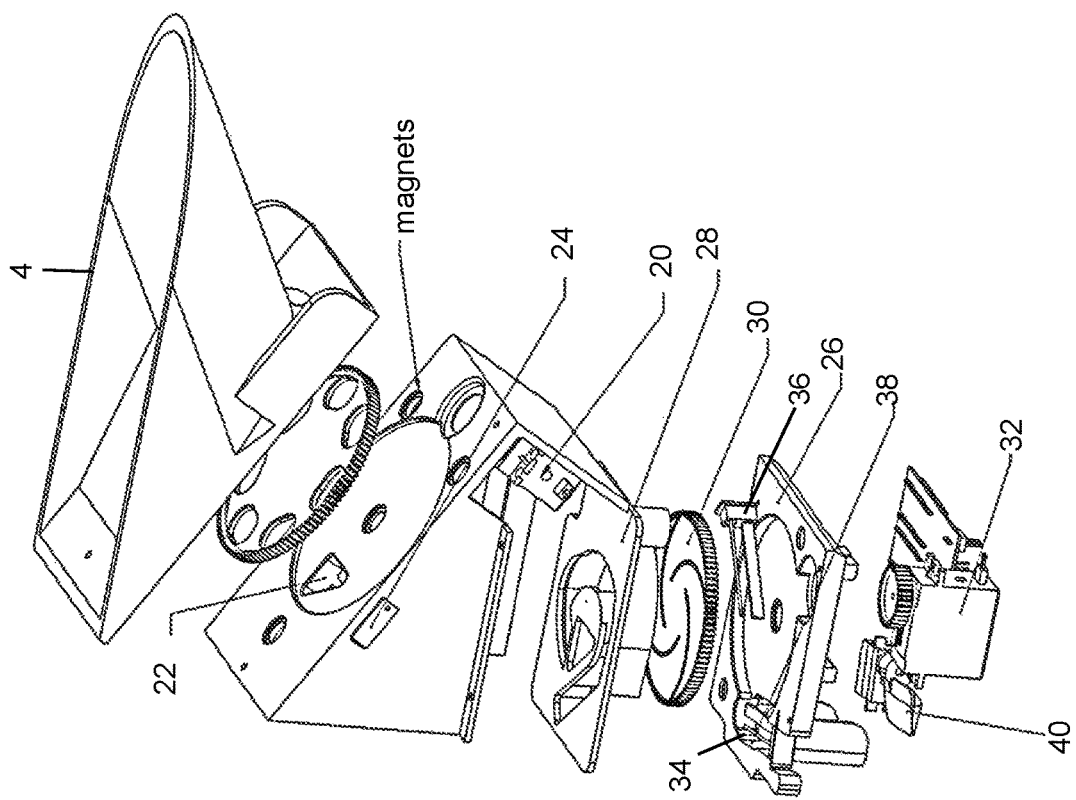
FIGS. 4A and 4B are exploded front left top (FIG. 4A) and back right top (FIG. 4B) views of the pill dispensing canister in FIG. 1C.
Figure 4A:
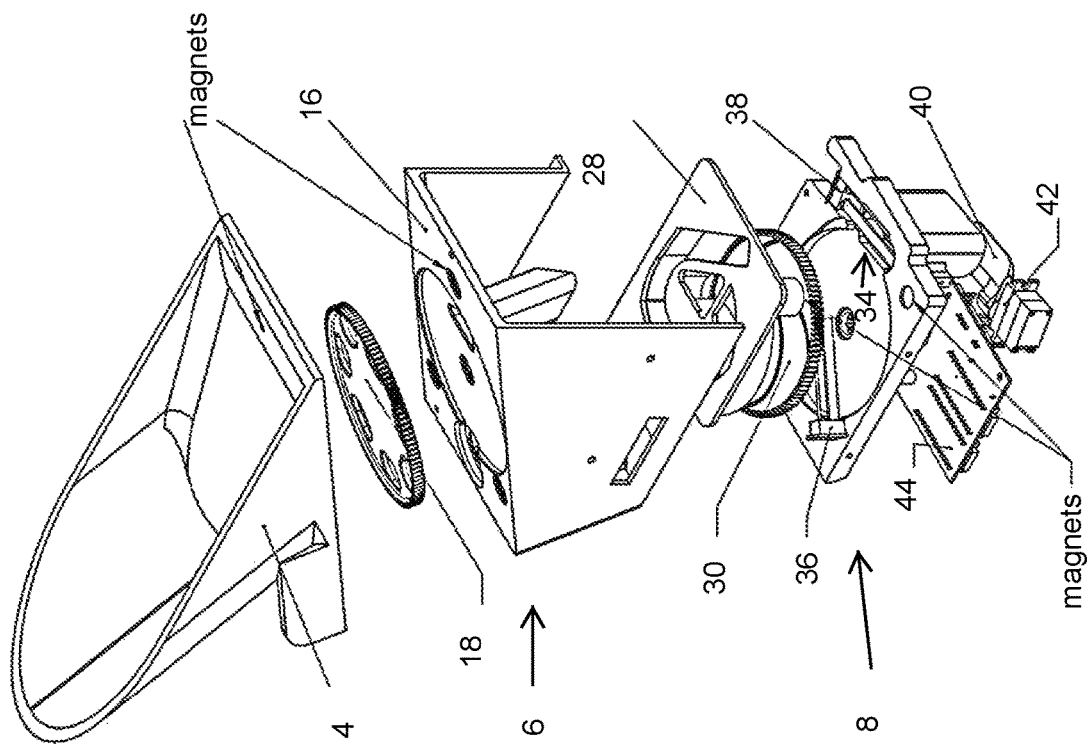
Figure 5:
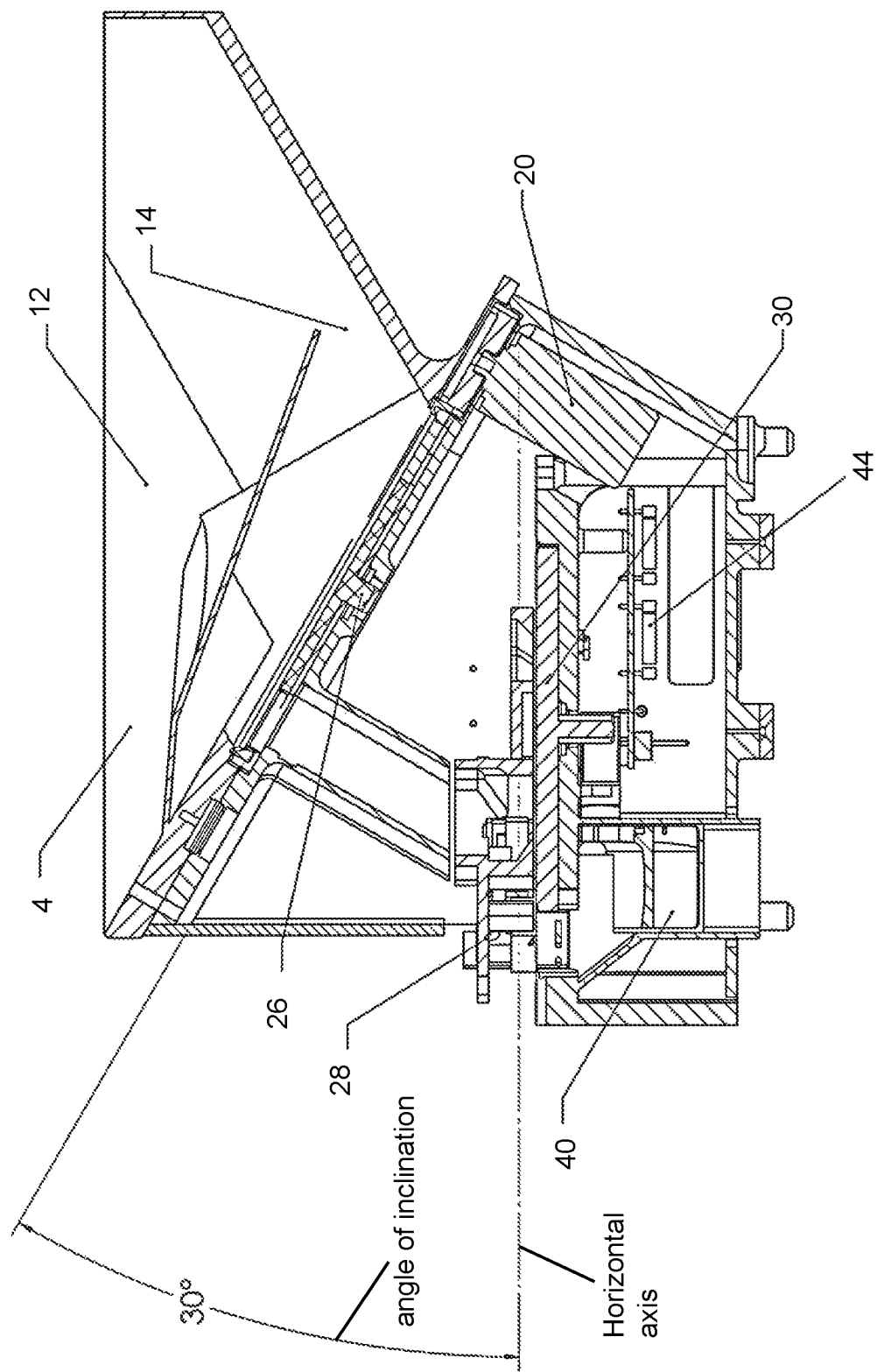
FIG. 5 is a cross sectional view of the pill dispensing canister of FIG. 1B along the section line F5.
Figure 6A:
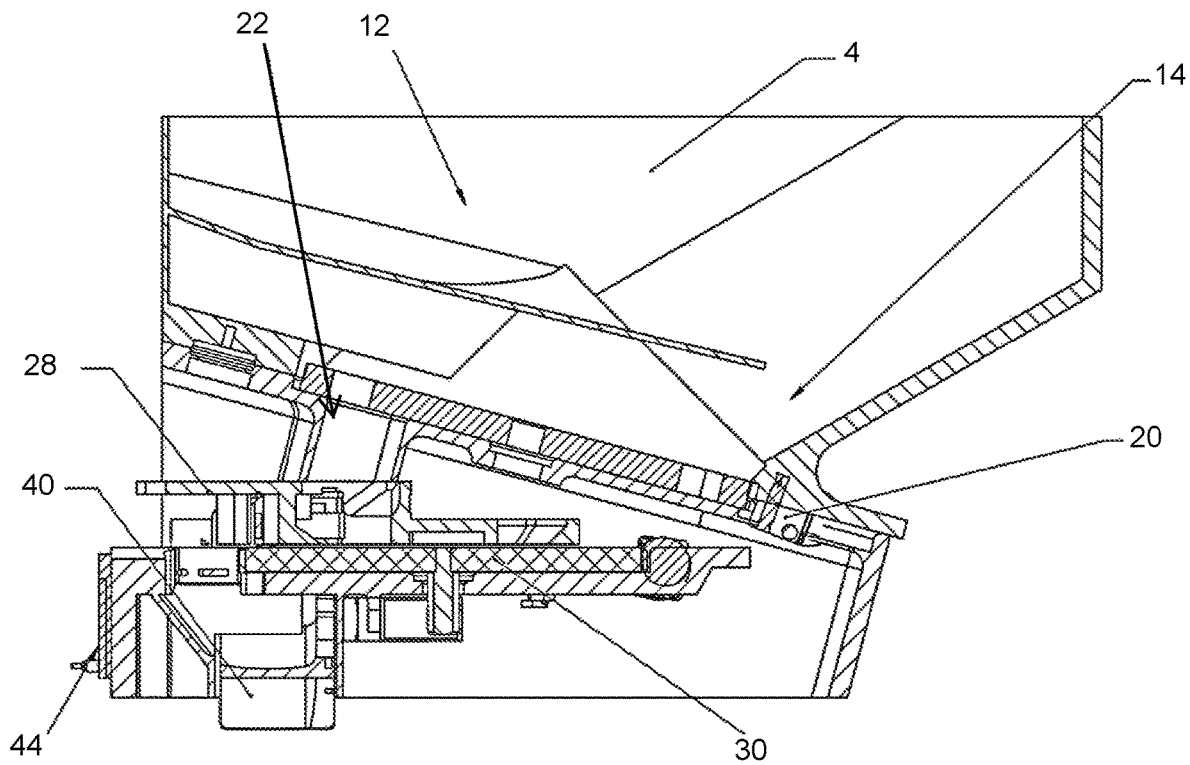
FIGS. 6A and 6B are cross sectional views of the pill dispensing canisters in FIGS. 1A and 1C respectively, along the sectional lines F6A and F6B respectively.
Figure 6B:
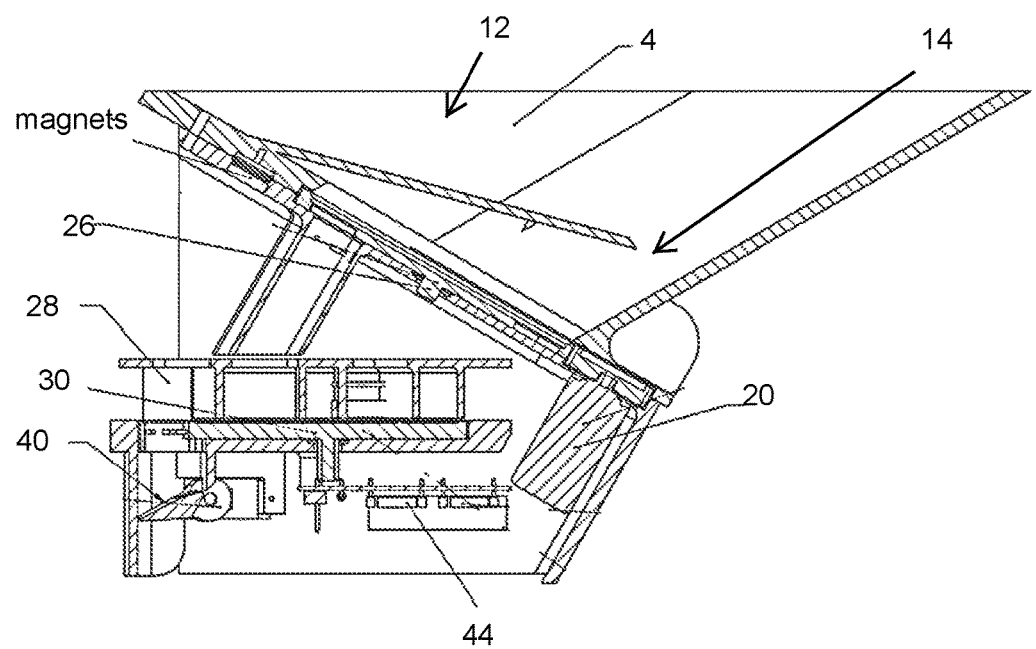
Figure 7A:
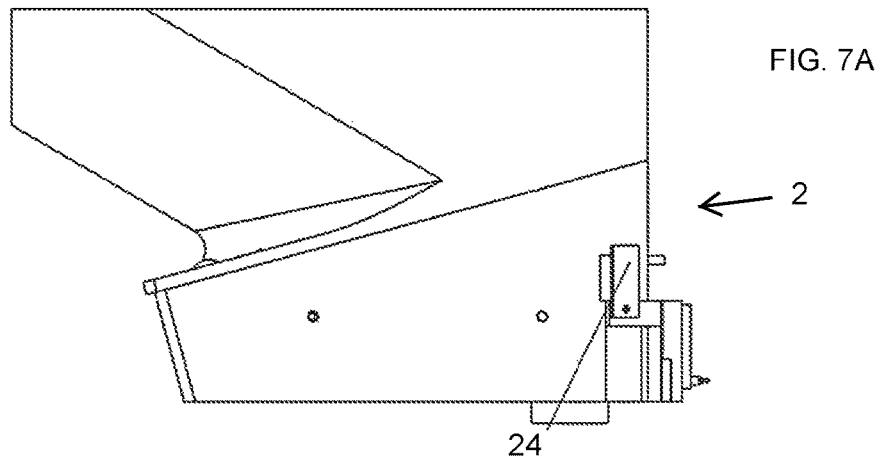
FIGS. 7A and 7B are left plan views of the pill dispensing canisters of FIGS. 1A and 1B respectively.
Figure 7B:
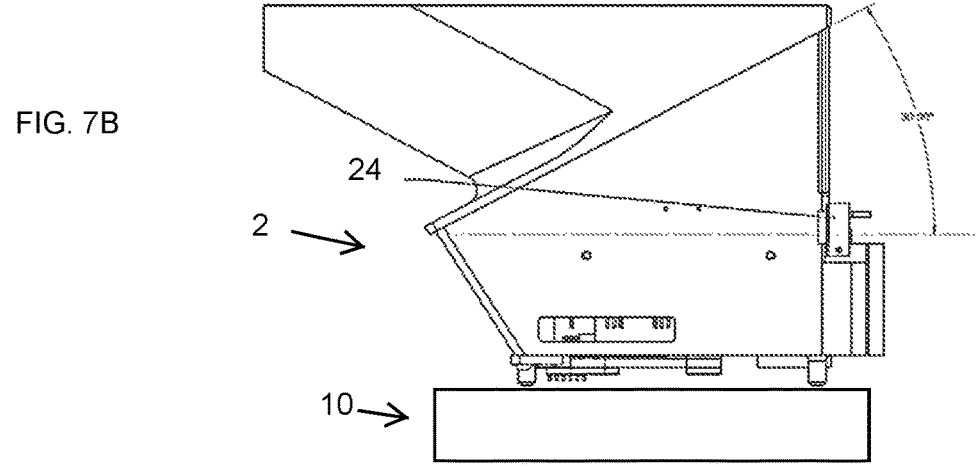
Figure 7C:
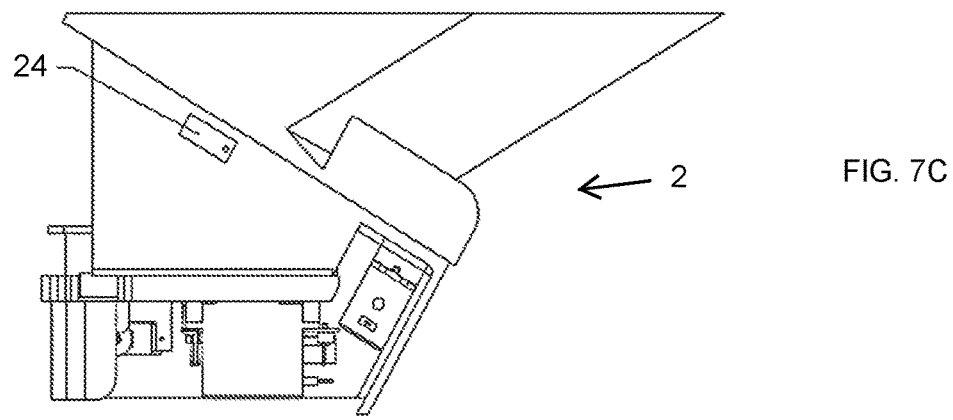
FIG. 7C is a right plan view of the canister of FIG. 1C.
Figure 9A:
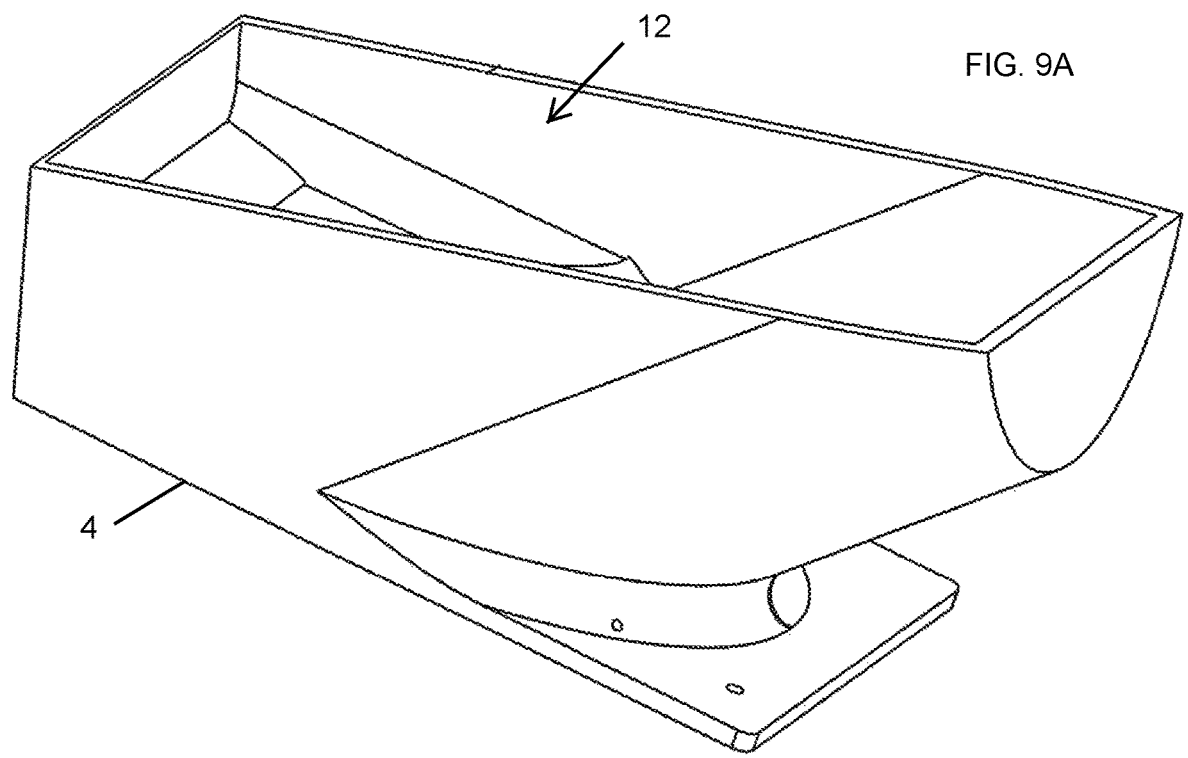
FIGS. 9A and 9B are respectively back right top and front left top isometric views of the hopper in the dispensing canister of FIG. 1A.
Figure 9B:
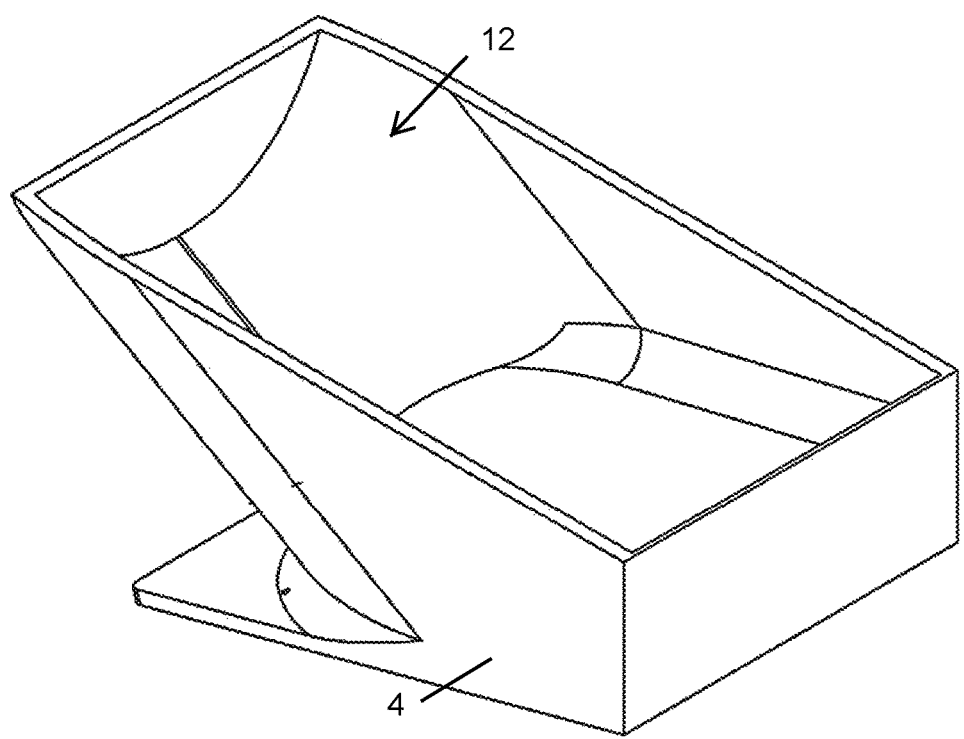
Figure 10A:
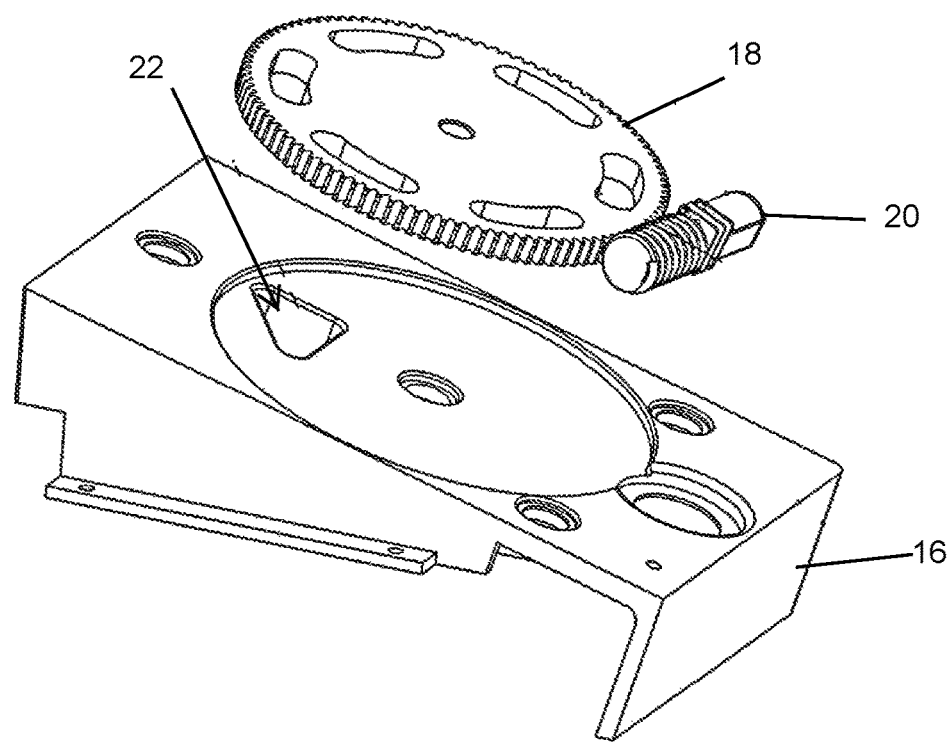
FIGS. 10A and 10B are exploded back and front views of the bulk dispensing disc of the dispensing canister of FIG. 1A.
Figure 10B:
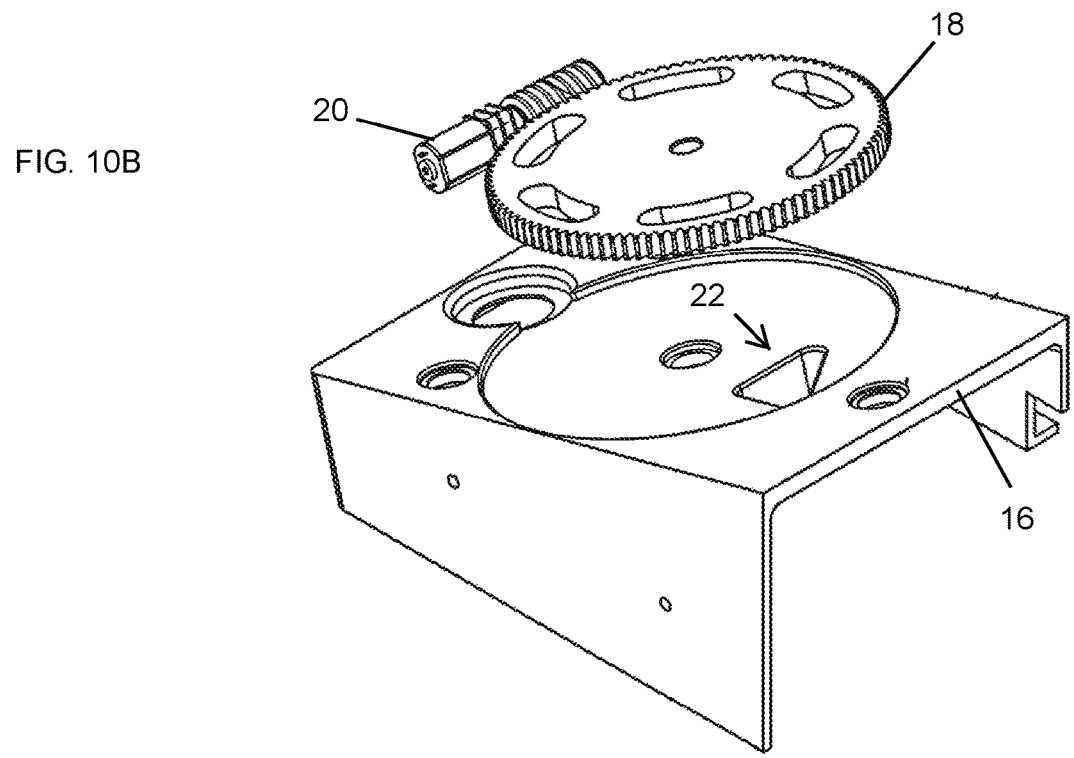
Figure 12B:
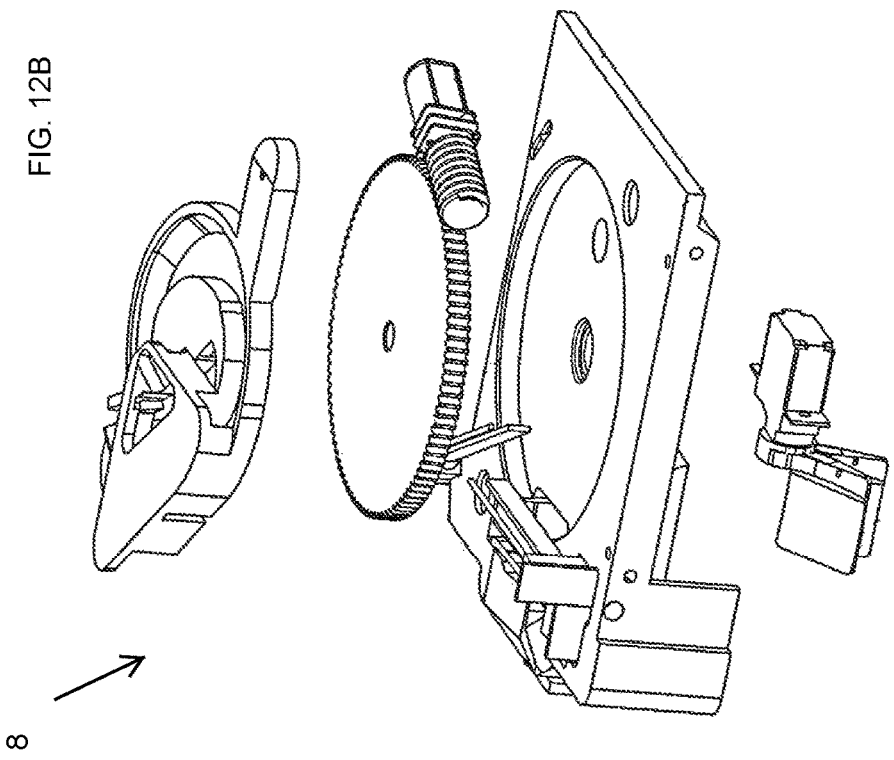
FIGS. 12A and 12B are exploded front left and side views, respectively, of the discrete dispenser of the dispensing canister of FIG. 1A.
Figure 12A:
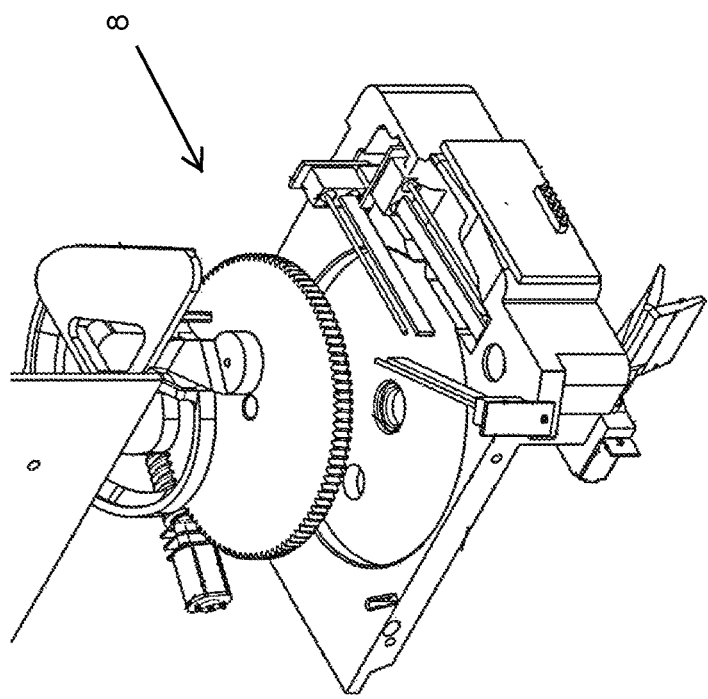
Figure 13:
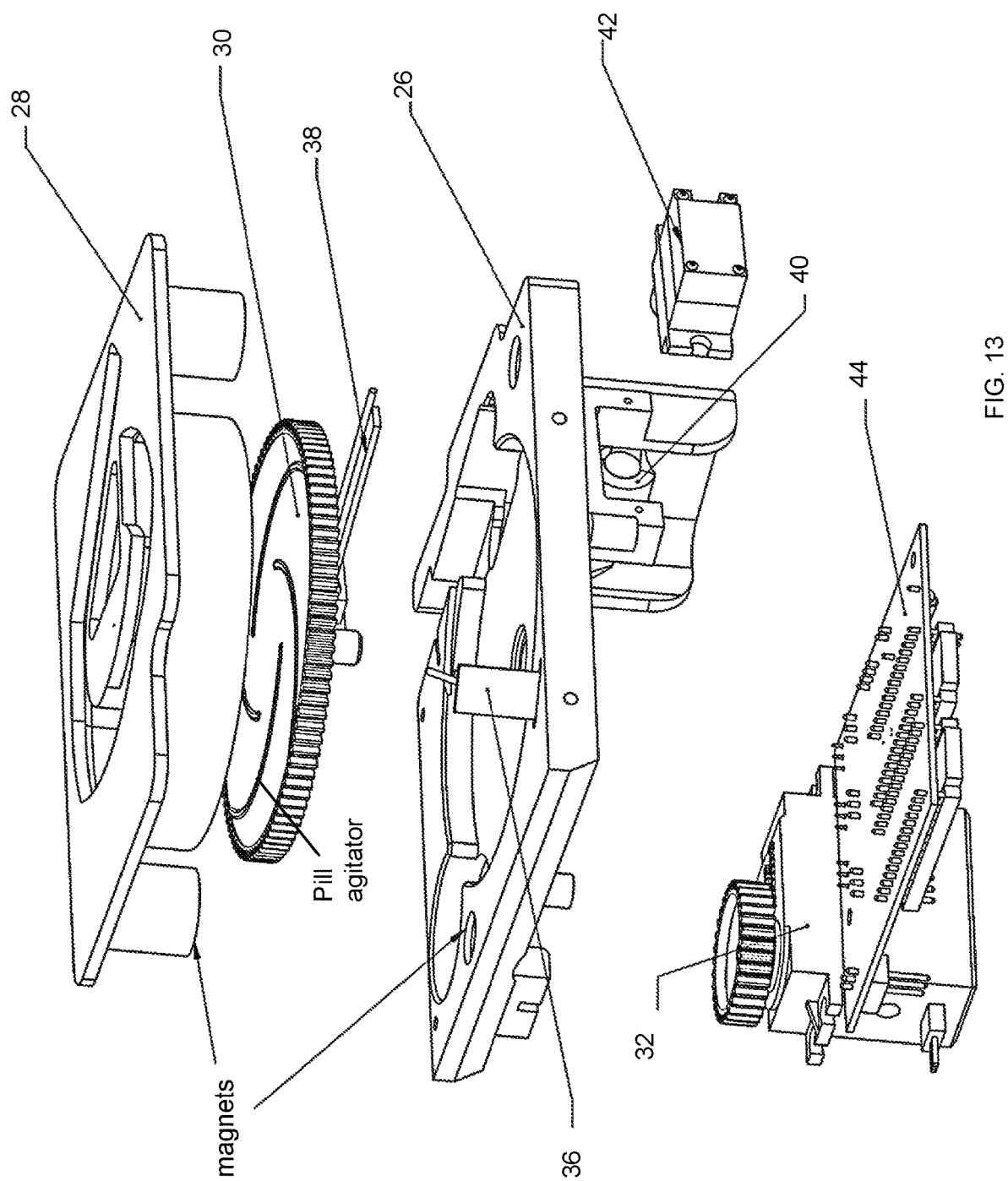
FIG. 13 is an exploded back right view of the discrete dispenser of the dispensing canister of FIG. 1C.
Figure 14:
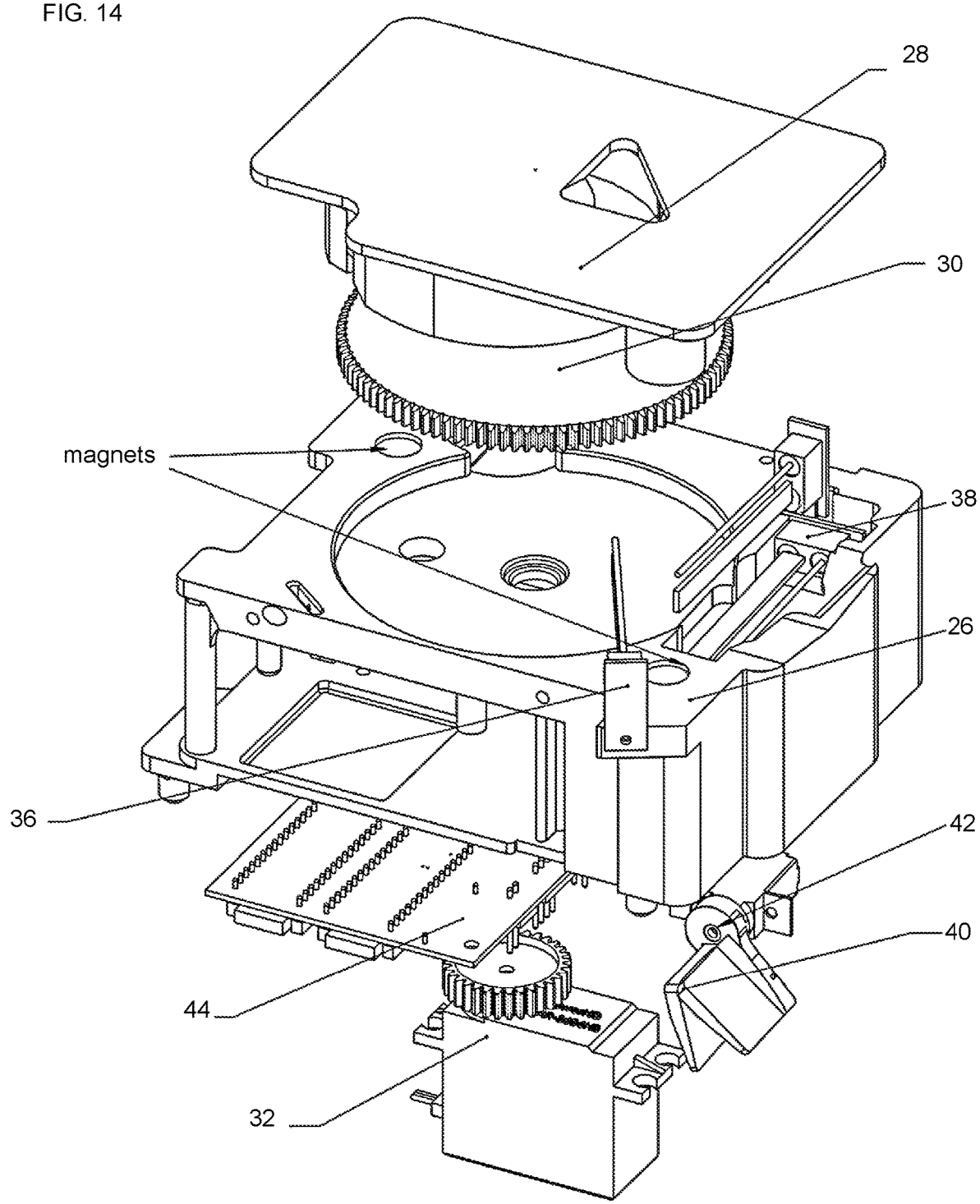
FIG. 14 is a an exploded front right view of the discrete dispenser of the dispensing canister of FIG. 1B.
Figure 15A:
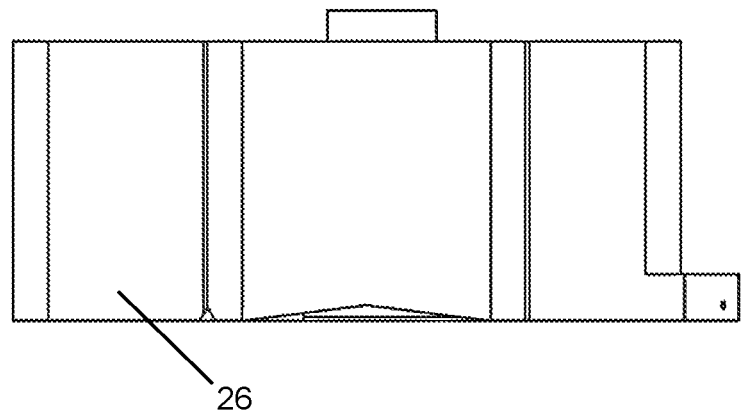
FIGS. 15A and 15B are side plan and top plan views of a discrete dispenser base of the dispensing canister of FIG. 1B.
Figure 15B:
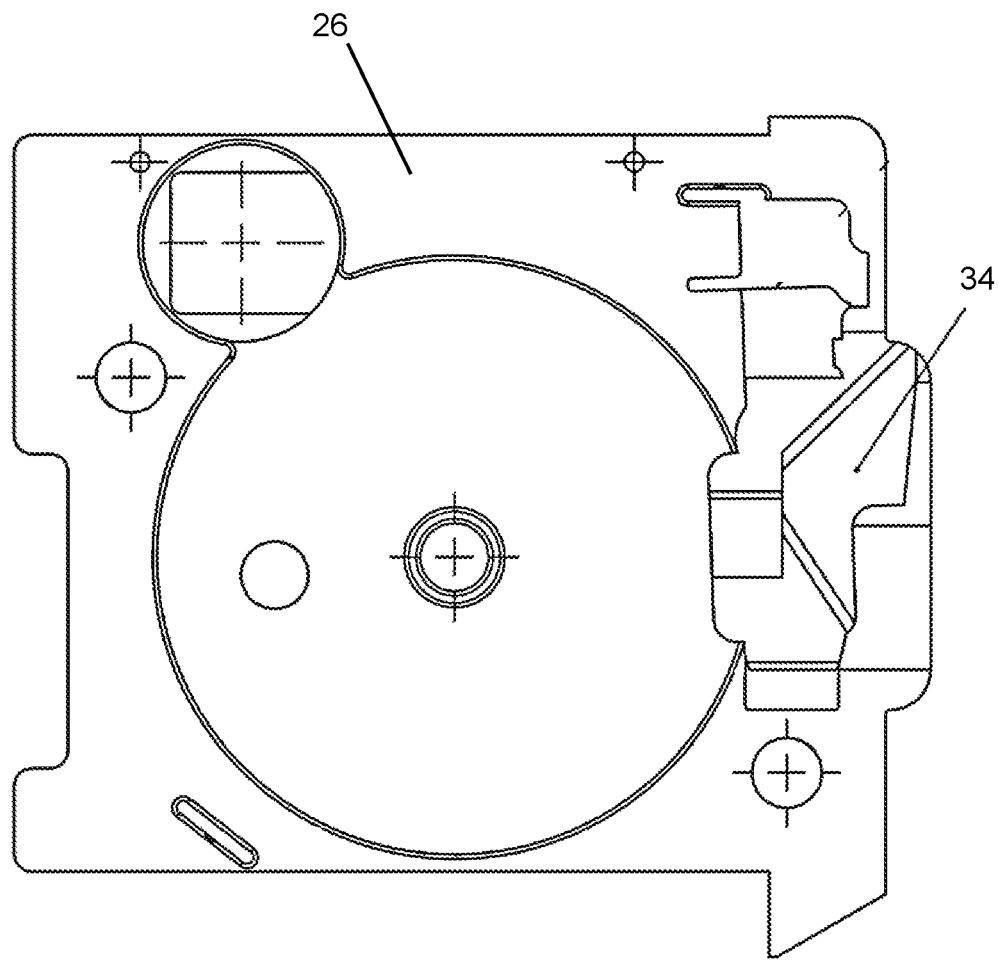
Figure 16B:
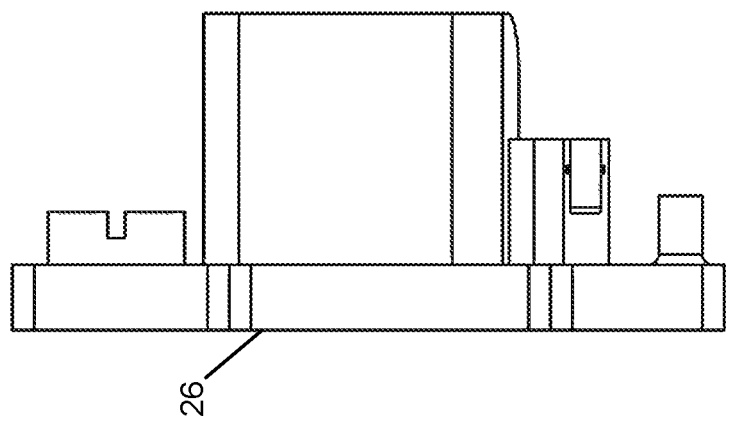
FIGS. 16A and 16B are side plan and top plan views of a discrete dispenser base of the dispensing canister of FIG. 1A.
Figure 16A:
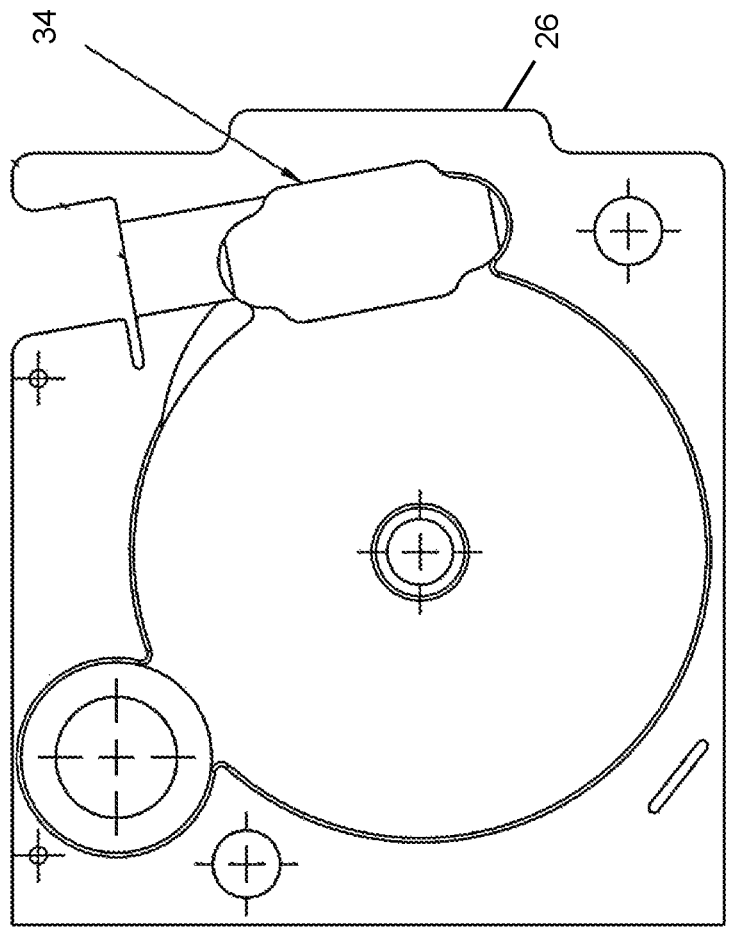

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1A-19B, a brief description concerning the various components of the present invention will now be briefly discussed. As can be seen in this embodiment, the pill dispensing canister system or pill dispensing canister 2 most generally comprises a hopper 4, a bulk dispenser 6, and a discrete dispenser 8, and is preferably mountable onto a pill encloser 10 of a pill packaging device, with the pill dispensing canister 2 functioning as a pill dispenser of the pill packaging device. The hopper 4 preferably includes a reservoir 12 and an initial passage 14. The bulk dispenser 6 preferably includes a bulk dispensing base 16, a bulk dispensing disc 18, a bulk dispensing motor 20, a pill exit chute 22, and a bulk dispensing sensor 24. The discrete dispenser 8 preferably includes a discrete dispensing base 26, a pill sorter 28, a discrete dispensing disc 30, a discrete dispensing motor 32, a pill drop chute 34, a pill jam sensor 36, a discrete pill sensor 38, a pill gate 40, a gate motor 42, and a control board 44.

The hopper 4 is preferably magnetically attached to a bulk dispenser 6. The reservoir 12 is a container for receiving a number of pills, preferably a large number of pills, such as between 1 and 10,000 pills, more preferably between 100 and 1,000 pills. The reservoir 12 shown has a large opening for ease of pouring pills into the reservoir 12, but the opening could be capped, or removably covered. The reservoir 12 could be designed such that pill containers, in an inverted position for example, securely fit onto the reservoir 12, by snap fit, screw fit, loose fit, running fit, or transition fit, for example. The reservoir 12 shown has a base and sides that are preferably positively angled with respect to the horizontal axis, such that pills will be urged from gravity to move toward the initial passage 14.

The initial passage 14 is preferably located at a lowest point of the hopper 4. The initial passage 14 is fluidly connected to the reservoir 12, and allows pills to fall or be moved from the reservoir 12 to the bulk dispenser 6. In the embodiment shown, the initial passage 14 is defined by a gap in the lower portion of the reservoir 12.

The bulk dispenser 6 preferably includes a bulk dispensing base 16, a bulk dispensing disc 18, a bulk dispensing motor 20, a pill exit chute 22, and bulk dispensing sensor 24. The bulk dispenser 6 is preferably magnetically mounted to the discrete dispenser 8.

The bulk dispensing base 16 provides support for the bulk dispenser 6, and with the hopper 4 forming a ceiling, contains pill that enter from the initial passage 14 within.

The bulk dispensing disc 18 is supported on the bulk dispensing base 16. The bulk dispensing disc 18 is preferably has at least one aperture defined in the surface of the disc, preferably proximate to a perimeter of the disc. In the embodiment show, six oblong apertures are defined in the disc. The bulk dispensing disc 18 is preferably aligned at a positive inclination angle to the horizon. In a first embodiment the inclination angle is preferably between 10 and 20 degrees, more preferably 15 degrees. In a second embodiment the inclination angle is preferably between 20 and 40 degrees, more preferably between 25 and 35 degrees, and most preferably 30 degrees. The apertures, with the bulk dispensing base 16 below the apertures, act to carry one or more pills in groups from a lower portion bulk dispenser 6 to an upper portion of the bulk dispenser 6, as the bulk dispensing disc 18 rotates. The pill exit chute 22 is defined in an upper portion of the bulk dispensing base 16 and preferably radially aligned with at least one of the bulk dispensing disc 18 apertures in at least one location along a rotation path of the bulk dispensing disc 18, preferably at or proximate to a highest location along the rotation path.

A bulk dispensing motor 20 turns the bulk dispensing disc 18. In the embodiments shown, the bulk dispensing disc 18 has toothed edges. The bulk dispensing motor 20 can thereby engage the toothed edges with a worm or pinion gear, for example, and impart an accurate amount of rotation on the bulk dispensing disc 18. A servo motor or dc gear motor, for example, may be used to drive the discs. In other embodiments, other gears may be used, or the edges of the bulk dispensing disc 18 and the dispensing motor gear may have rubber or another high friction surface and no teeth, for example. The discrete dispensing disc 30 may be similarly actuated by discrete dispensing motors 32 of various types and with various gears.

A pill exit chute 22 is defined in the bulk dispensing base 16 as described above, and provides a path for pills carried by an aperture in the bulk dispensing disc 18 to a from a first location proximate to the initial passage 14 to a second location proximate to the pill exit chute 22 inlet, through the pill exit chute 22, and out from the pill exit chute 22 outlet to the discrete dispenser 8. The terminal portion of the pill exit chute 22 outlet is preferably aligned with the pill sorter 28 entrance.

The bulk dispensing sensor 24 is preferably mounted in a side of the bulk dispensing base 16.

The discrete dispenser 8 preferably includes a discrete dispensing base 32, a pill sorter 28, a discrete dispensing disc 30, a discrete dispensing motor 32, a pill drop chute 34, a pill jam sensor 36, a discrete pill sensor 38, a pill gate 40, a gate motor 42, and a control board 44. The discrete dispenser 8 is preferably removably attached to a pill enclosure housing, through preferably magnetic attachment, but also or alternatively be attached through other preferably mechanical attachments, such as latches, clips, straps, Velcro, snap fit, or bolted together, or post and hole fit.

The discrete dispensing base 32 supports the various components of the discrete dispenser 8, and preferably is designed to securely, but releasably fit onto an upper housing of a pill ensloser 10 of a pill packaging device.

Figure 18A:
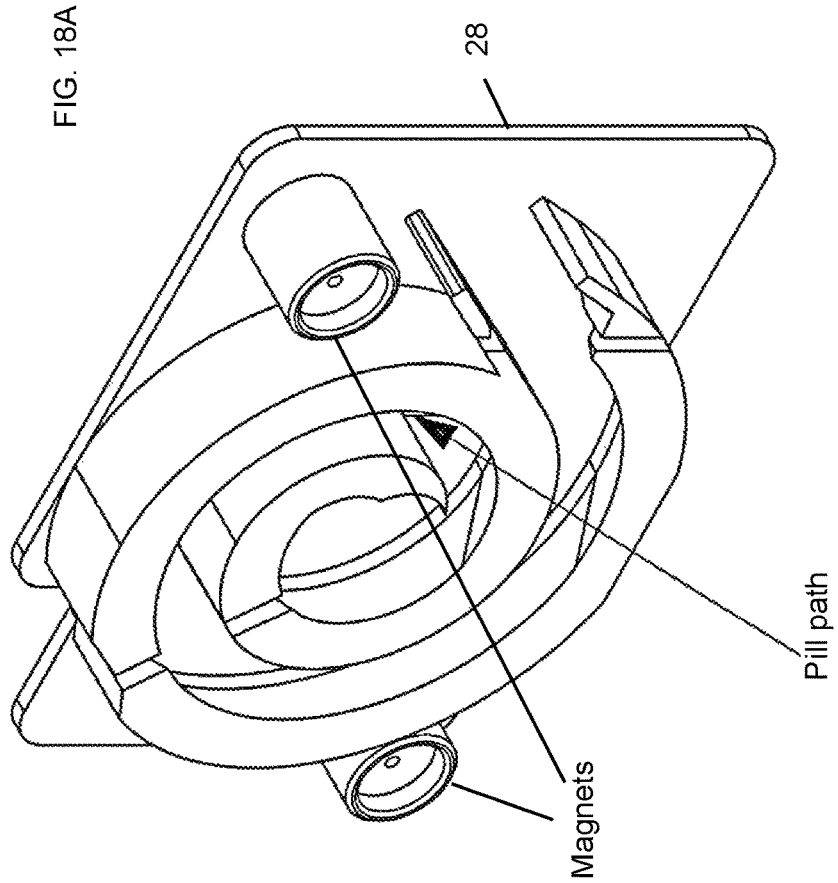
FIG. 18A is an isometric view and FIG. 18B is a bottom plan view of a larger pill sized pill sorter.
Figure 18B:
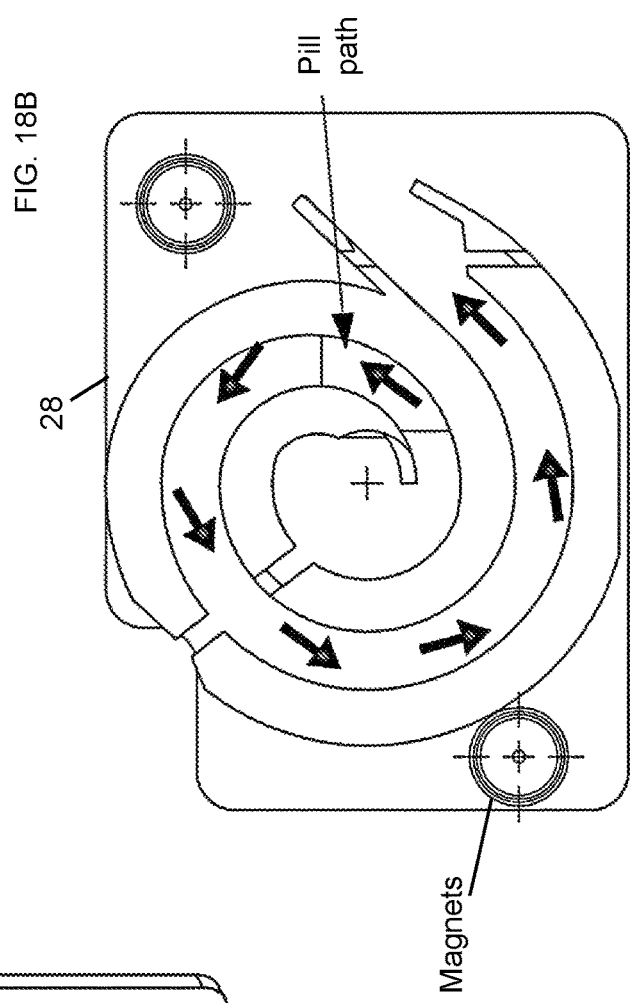
Figure 19B:
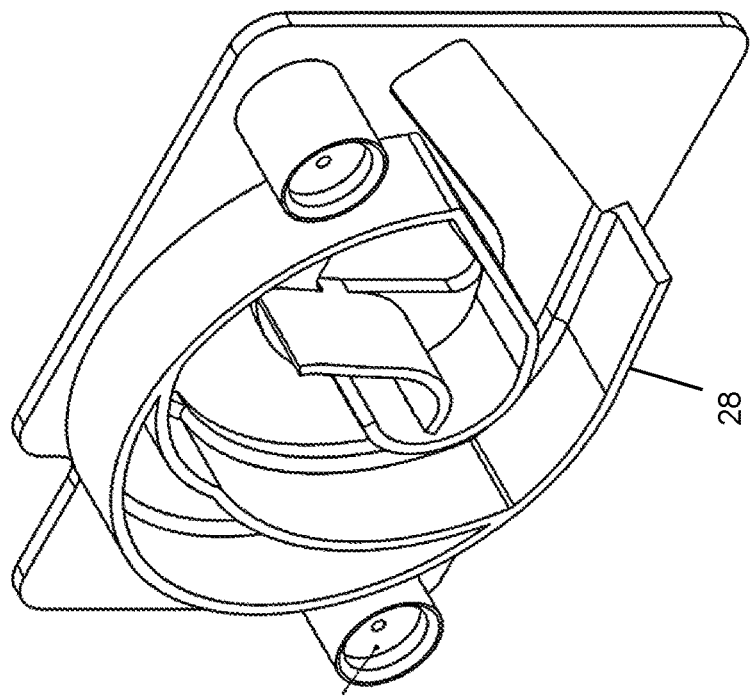
FIG. 19A bottom plan view and FIG. 19B is an isometric view of an additional pill sorter.
Figure 19A:
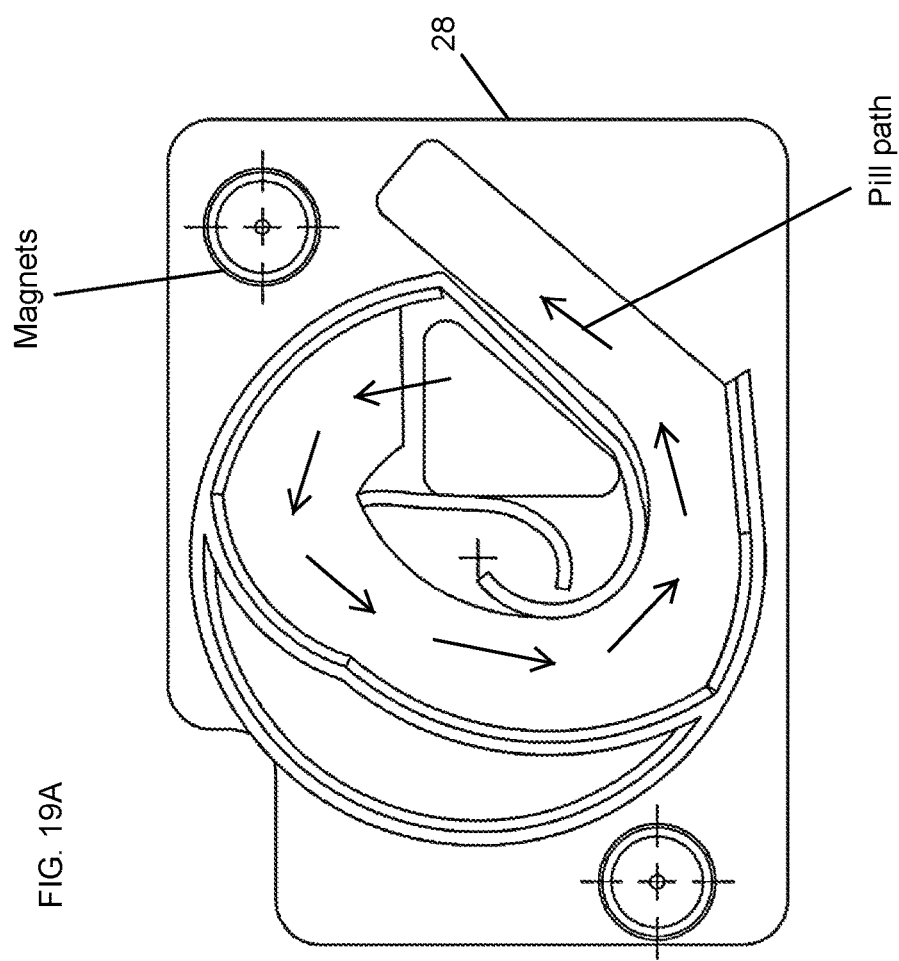

The pill sorter 28 is preferably magnetically mounted on top of the discrete dispensing base 32. Two different pill sorters 28 are shown. In FIGS. 17A-17C, a first pill sorter 28 is preferably used to sort up to medium size pills, for example up to 0.375 inch wide pills. In FIGS. 18A and 18B, a second pill sorter 28 is preferably used to sort pills larger than 0.375 inch wide. The sorting shape results in no calibration being required for each pill.

A discrete dispensing disc 30 mounted in the discrete dispensing base 32, and moves beneath the pill sorter 28 to move pills along a pill path through the pill sorter 28. The discrete dispensing disc 30 may have smooth or rough top surface, and may have raised portions that act as pill agitators to gently move pills and loosen any piles of pills in the pill sorter 28.

The discrete dispensing motor 32 turns the discrete dispensing disc 30.

The pill drop chute 34 is defined in the discrete dispensing base 32, and leads to the entrance of the pill encloser, preferably a pill funnel.

The pill jam sensor 36 disposed on the discrete dispensing base 32, and the discrete pill sensor 38 is disposed adjacent to the pill drop chute 34.

The pill gate 40 selectively blocks passage of the pills in the pill drop chute 34. The gate motor 42 selectively moves the pill gate 40 between open and closed positions.

The control board 44 receives information from the sensors, control the motors, and communicate with the pill packaging device.

Though the bulk dispensing discs 18 and pill sorters 28 many handle a range of pill sizes, in some embodiments they may be designed to handle relatively larger or smaller pills. In some embodiments, extra bulk dispensing discs 18 may be included in the pill dispensing canister 2, some bulk dispensing discs 18 having smaller apertures for smaller pills, some with medium sized apertures for medium sized pills, and/or some with larger sized apertures for larger sized pills. Additionally, in some embodiments, extra pill sorters 28 be included in the pill dispensing canister 2, some pill sorters 28 having smaller pathways for smaller pills, some with medium sized pathways for medium sized pills, and some with larger sized pathways for larger sized pills.

In some embodiments, the pill dispensing canister 2 is electrically connected to the pill packaging device, such that information and or power may be transferred vial electrical wired connection one way or both ways between the device and canister. In other embodiments, the pill dispensing canister 2 is wirelessly connected to the pill packaging device, such that information and or power may be transferred wirelessly (e.g., Bluetooth and/or wifi data connection and/or inductive charging)

The following is one embodiment for a process for the functioning of pill dispensing canister 2. The following order of steps is preferable, but not necessarily required to complete the process, some steps may be run sequentially or overlap with other steps, and in some embodiments some of the steps may be omitted or substituted with other steps First, with the pill dispensing canister 2 mounted on and electrically connected to the pill packaging device, pills from a stock bottle are poured in to the hopper 4, preferably until the reservoir 12 is full or the stock bottle is empty. The pills will naturally move in the reservoir 12 and into the initial passage 14, with some resting on the bulk dispenser disc and some in the apertures of the bulk dispensing disc 18. Second, the PLC from the pill packaging device sends a start command to a pill counter of the control board 44. Third, the bulk dispensing motor 20 starts to rotate. This causes the bulk dispensing disc 18 to rotate, carrying pills in the bulk dispensing disc 18 apertures around the rotation paths of the disc and the apertures until the disc aperture moves over the pill exit chute 22 (preferably around at a vertically highest point of the aperture's rotation path) and the pills drop from the bulk dispenser disc aperture in and through the pill exit chute 22 and then into the pill sorter 28. As one or more pills drop through the pill exit chute 22, the bulk dispensing sensor 24 counts the pill drops and stores the pill drop counts in Counter #1. The bulk dispensing motor 20 continues to run until the sorting chamber has 5 or more pills in it. Fourth, the discrete dispensing motor 32 starts to rotate. The pills which have fallen into the pill sorter 28 are moved by the rotating discrete dispensing disc 30, and agitated by pill agitators on the surface of the discrete dispensing disc 30, along a serpentine path which causes the pills to separate from one another and move along the path defined by the pill sorter 28, preferably from an inner radial location to an outer radial location, and ultimately to the pill drop chute 34 to drop one pill at a time in the pill drop chute 34. Fifth, the discrete dispensing sensor mounted adjacent to the pill drop chute 34 senses the pill dropped into the pill drop chute 34, dropping a distance in the pill drop chute 34 and coming to a rest on the pill gate 40, the single dispensing motor stops and the control board 44 subtracts "one" from Counter #1 and adds "one" to counter #2. Sixth, the bulk dispensing motor 20 starts rotating to drop pills in to pill sorter 28 if the Counter #1 is less than 5. Seventh, the PLC of the pill packaging device sends a pill drop command to drop the pill from pill drop chute 34. Eighth, the gate motor 42 rotates the pill gate 40, preferably 90 degrees, to open the pathway of the pill drop chute 34 and allow the pill to drop through the pill drop chute 34 and into the pill packaging device (preferably into the pill funnel), and the control board 44 subtracts "one" from Counter #2. Ninth, the gate motor 42 rotates the pill gate 40 back to close the pathway for the pill drop chute 34. Tenth, steps three through nine are repeated until the control board 44 receives a stop command from PLC of the pill packaging device. Eleventh, the PLC of the pill packaging device sends stop command to control board 44 to halt all pill dispensing operations. Twelfth, the user may pick up the hopper 4 and pour the remaining pills in the bill hopper 4 back in to the stock bottle.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, I claim:

1. A pill dispensing canister mountable onto a pill packaging device comprising:
    a hopper;
    a bulk dispenser; and
    a discrete dispenser;
    wherein the bulk dispenser includes a bulk dispensing base, a bulk dispensing disc, a bulk dispensing motor, a pill exit chute and a bulk dispensing sensor.
2. The pill dispensing canister of claim 1 wherein the bulk dispensing disc has toothed edges that are driven by the bulk dispensing motor.
3. The pill dispensing canister of claim 1 wherein a terminal portion of the pill exit chute outlet is aligned with a pill sorter entrance in the discrete dispenser.
4. The pill dispensing canister of claim 1 wherein the bulk dispensing sensor is mounted in a side of the bulk dispensing base.
5. The pill dispensing canister of claim 1 wherein the hopper includes a reservoir to hold more than 100 pills and an initial passage that lead from the reservoir the bulk dispenser.
6. The pill dispensing canister of claim 1 wherein the bulk dispensing disc has at least one aperture defined in a surface of the bulk dispensing disc.
7. The pill dispensing canister of claim 6 wherein the at least one aperture is proximate to a perimeter of the bulk dispensing disc.
8. The pill dispensing canister of claim 6 wherein the bulk dispensing disc is aligned at an inclination angle to the horizon of between 10 degrees and 40 degrees.
9. The pill dispensing canister of claim 7 wherein at least 4 apertures are defined in the surface of the bulk dispensing disc and the apertures are non-circular in shape.
10. The pill dispensing canister of claim 6 wherein the pill exit chute is defined in an upper portion of the bulk dispensing base.
11. The pill dispensing canister of claim 10 wherein the pill exit chute is radially aligned with at the least one aperture of the bulk dispensing disc in at least one location along a rotation path of the bulk dispensing disc.
12. The pill dispensing canister of claim 11 wherein the pill exit chute is radially aligned with at the least one aperture of the bulk dispensing disc at or proximate to a highest location along the rotation path.
13. A pill dispensing canister mountable onto a pill packaging device comprising:
    a hopper;
    a bulk dispenser; and
    a discrete dispenser;
    wherein the hopper is releasably magnetically attached to the bulk dispenser and the bulk dispenser is releasably magnetically attached to the discrete dispenser, and the discrete dispenser is releasably attachable to a pill enclosure housing.
14. A pill dispensing canister mountable onto a pill packaging device comprising:
    a hopper;
    a bulk dispenser; and
    a discrete dispenser;
    wherein the discrete dispenser includes a discrete dispensing base, a pill sorter, a discrete dispensing disc, a discrete dispensing motor, a pill drop chute, a pill jam sensor, a discrete pill sensor, a pill gate, a gate motor, and a control board.
15. The pill dispensing canister of claim 14 wherein the discrete dispensing disc is mounted in the discrete dispensing base, and rotates beneath the pill sorter to move pills along a pill path through the pill sorter from an entrance at a terminal portion of a pill exit chute of the bulk dispenser to an exit at a pill drop chute, the discrete dispensing disc having toothed edges that are driven by a discrete dispensing motor.
16. The pill dispensing canister of claim 14 wherein the pill jam sensor is disposed on the discrete dispensing base, and the discrete pill sensor is disposed adjacent to the pill drop chute.
17. The pill dispensing canister of claim 14 wherein the pill gate selectively blocks passage of pills in the pill drop chute, and the gate motor selectively moves the pill gate between open and closed positions.
18. The pill dispensing canister of claim 14 wherein the pill sorter defines a serpentine pill path, and the pill sorter is magnetically mounted on top of the discrete dispensing base.
19. A pill dispensing canister mountable onto a pill packaging device comprising:
    a hopper; a bulk dispenser; a discrete dispenser; the hopper including a reservoir to hold more than 100 pills and an initial passage that lead from the reservoir the bulk dispenser; the bulk dispenser including a bulk dispensing base, a bulk dispensing disc, a bulk dispensing motor, a pill exit chute and a bulk dispensing sensor; the bulk dispensing disc having six oblong shaped apertures defined in a surface of the bulk dispensing disc, proximate to a perimeter of the bulk dispensing disc; the bulk dispensing disc being aligned at an inclination angle to the horizon of between 10 degrees and 40 degrees; the pill exit chute being defined in an upper portion of the bulk dispensing base and radially aligned with at the least one aperture of the bulk dispensing disc in at least one location along a rotation path of the bulk dispensing disc at or proximate to a highest location along the rotation path; the bulk dispensing disc having toothed edges that are driven by the bulk dispensing motor; a terminal portion of the pill exit chute outlet is aligned with a pill sorter entrance in the discrete dispenser;

the bulk dispensing sensor is mounted in a side of the bulk dispensing base; the hopper being releasably magnetically attached to the bulk dispenser and the bulk dispenser being releasably magnetically attached to the discrete dispenser, and the discrete dispenser being releasably attachable to a pill enclosure housing; the discrete dispenser includes a discrete dispensing base, a pill sorter, a discrete dispensing disc, a discrete dispensing motor, a pill drop chute, a pill jam sensor, a discrete pill sensor, a pill gate, a gate motor, and a control board; the discrete dispensing disc is mounted in the discrete dispensing base, and rotates beneath the pill sorter to move pills along a pill path through the pill sorter from an entrance at a terminal portion of a pill exit chute of the bulk dispenser to an exit at a pill drop chute; the discrete dispensing disc having toothed edges that are driven by a discrete dispensing motor; the pill jam sensor being disposed on the discrete dispensing base; the discrete pill sensor is disposed adjacent to the pill drop chute; the pill gate selectively blocks passage of pills in the pill drop chute, and the gate motor selectively moves the pill gate between open and closed positions; the pill sorter defines a serpentine pill path, and the pill sorter is magnetically mounted on top of the discrete dispensing base; and the control board receives signals from the sensors and controls the motors.

* * * * *